United States Patent [19]

Scherer

[11] Patent Number: 5,020,179
[45] Date of Patent: Jun. 4, 1991

[54] ELECTRIC TOOTHBRUSH

[75] Inventor: Benjamin Scherer, Zürich, Switzerland

[73] Assignee: Gimelli & Co. AG, Zollikofen, Switzerland

[21] Appl. No.: 461,290

[22] Filed: Jan. 5, 1990

[30] Foreign Application Priority Data

Jan. 11, 1989 [DE] Fed. Rep. of Germany ....... 8900234

[51] Int. Cl.⁵ .............................................. A46B 13/02
[52] U.S. Cl. ..................................... 15/22.1; 15/176.5
[58] Field of Search ................... 15/22 R, 22 C, 28, 29

[56] References Cited

U.S. PATENT DOCUMENTS

| | | |
|---|---|---|
| 2,215,031 | 9/1940 | Elmore . |
| 3,160,902 | 12/1964 | Aymar . |
| 3,193,864 | 7/1965 | Makowsky . |
| 3,478,433 | 11/1969 | Richmond . |
| 4,156,620 | 5/1979 | Clemens ............................ 15/22 R |
| 4,432,729 | 2/1984 | Fattaleh . |
| 4,545,087 | 10/1985 | Nahum ............................ 15/22 R |
| 4,827,550 | 5/1989 | Graham et al. . |
| 4,845,795 | 7/1989 | Crawford et al. .................. 15/22 R |

FOREIGN PATENT DOCUMENTS 3406112 8/1985 Fed. Rep. of Germany .
3630499 3/1988 Fed. Rep. of Germany .
1525112 5/1968 France .

OTHER PUBLICATIONS

Getriebetechnik Lehrbuch, Volmer et al., pp. 53–55 and 72–73.

Primary Examiner—Edward L. Roberts
Attorney, Agent, or Firm—Wegner, Cantor, Mueller & Player

[57] ABSTRACT

An electric toothbrush comprises a manually guided handle and a brush member having a brush head with a plurality of separately rotating bristle holders which are connected in the brush head to gearing driving them. The bristle holders are mounted in an insert which is insertable into the brush head in a releasable manner so as to be easily exchangeable by the user. Each of the bristle holders has a coupling element in the form of a cam which is insertable, by way of a plug-in connection, in a respective groove in a connecting rod which is connected to a drive means in the handle.

5 Claims, 3 Drawing Sheets

ELECTRIC TOOTHBRUSH

BACKGROUND OF THE INVENTION

The invention relates to an electric toothbrush with a handle which is to be manually guided and with a brush member which has a brush head with several, separately rotating bristle holders which, in the brush head, are connected to gearing for driving them, and in which a component comprising the brush member is connected to the toothbrush so as to be easily exchangeable by the user. EP-O 254 397 relates to such a toothbrush.

As electric toothbrushes of this type are generally used by several people and as the bristles are subject to wear, it is necessary for them to be arranged on a component which can be easily exchanged by the user. According to the above-mentioned EP-O 254 397, the brush member is fixed detachably as a whole on the handle. In conventional electric toothbrushes, in which the brush member merely has to perform an oscillating and/or a to-and-fro movement, the brush member is a relatively simple component, so that exchange thereof involves low costs. With the toothbrush according to EP-O 254 397, however, a total of ten gear wheels driving the bristle holders are arranged in the brush head of the brush member and are driven by a toothed rack which is axially movable in the brush member. The toothed rack is provided with a coupling which, when the bristle holder is placed on the handle, couples to a connecting rod provided therein. Owing to these components which are required in the brush member and form gearing, the brush member is relatively expensive overall, exchange thereof entailing considerable costs.

SUMMARY OF THE INVENTION

The object of the invention is to develop an electric toothbrush such that the exchange of its component comprising the bristle holders involves minimum costs.

According to the invention, this object is achieved in that the component is an insert in which the bristle holders are mounted, and which can be inserted into the brush head, and in that the bristle holders each comprise a coupling element which can be coupled to the gearing by a plug-in connection.

Owing to this design according to the invention, the bristle holders with the bristles are provided on a component which is very simple and can therefore be produced inexpensively. This component merely has rotatably mounted bristle holders without gearing. Several such components can therefore be provided so that the toothbrush can be used by various people or the bristles can also be replaced with low expenditure. The toothbrush is particularly simple in construction if the brush head has a receiver which is open on one side, for holding the insert, and if a manually releasable snap connection is provided for fixing the insert.

The invention could be carried out with the toothbrush according to EP-O 254 397, in which the gearing comprises a toothed rack and several gear wheels. A coaxial peg of each individual bristle holder is engaged in a receiver in an associated gear wheel. However, the overall construction of the toothbrush is simpler if the gearing has a connecting rod comprising transverse grooves in the region of the brush head and if the coupling element is formed in each case by a cam which is arranged on the bristle holder and engages in a transverse groove after insertion of the insert.

Numerous embodiments of the invention are possible. One possible embodiment is illustrated in the drawings to clarify the underlying principle of the invention and is described below.

DESCRIPTION OF PREFERRED EMBODIMENT

Figure 1:
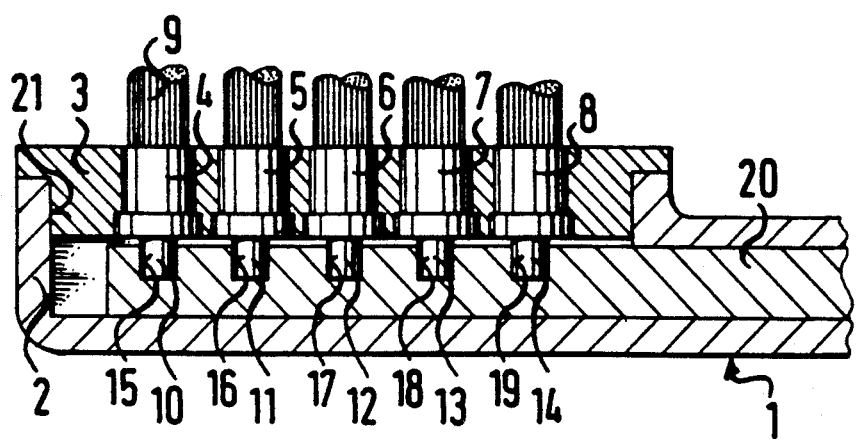
FIG. 1 shows a longitudinal section through a front region of a brush member of a toothbrush according to the invention.

FIG. 1 shows a brush member 1 which forms a brush head 2 at its front end. In this brush head 2, there is inserted exchangeably from above an insert 3 in which several bristle holders 4–8 with tufts of bristles 9 are rotatably mounted. Each bristle holder 4–8 has a cam 10–14 which, in FIG. 1, projects downward out of the insert 3 and engages in each case in a transverse groove 15–19 in a connecting rod 20 arranged axially movably in the brush member 1. It is important for the invention that the insert 3 can be inserted in an easily releasable manner into a receiver 21 in the brush head 2. If the insert 3 is pulled out of the receiver 21, the cams 10–14 will slide out of the upwardly open transverse grooves 15–19.

Figure 2:
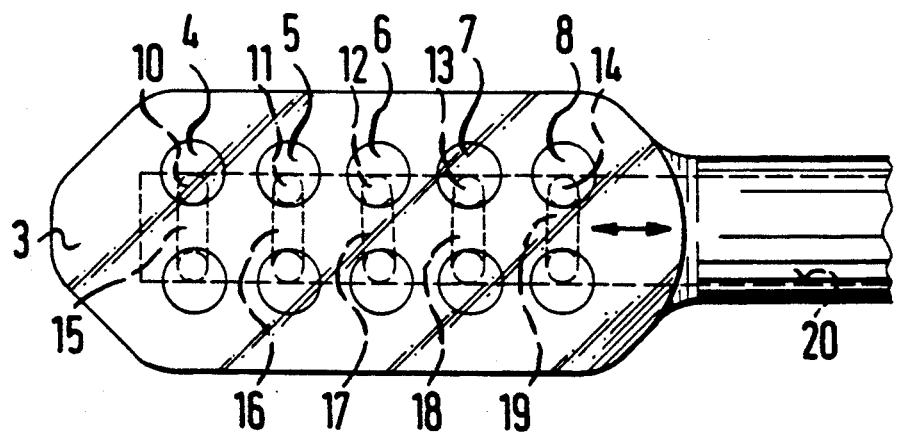
FIG. 2 shows a plan view of the brush member.

In FIG. 2, the transverse grooves 15–19 are shown in broken lines. The cams 10–14 engaged, therein as well as the cams of an additional row of bristle holders are also shown. If the connecting rod 20 performs a reciprocating movement, the engagement of the cams 10–14 and of the additional cams in the transverse grooves 15–19 will cause a rotational movement of all bristle holders 4–8 as well as the additional unnumbered bristle holders.

Figure 3:
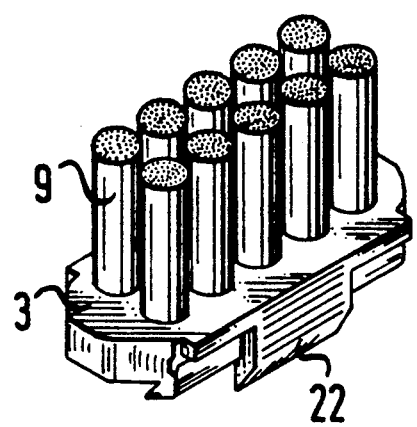
FIG. 3 shows a perspective view of an insert for the brush member.

FIG. 3 shows, on the insert 3 comprising the tufts of bristles 9, a side catch 22 with which the insert 3 can be snapped in the receiver 21.

Figure 4:
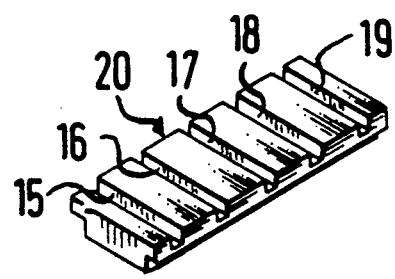
FIG. 4 shows a perspective view of a front region of a connecting rod of the brush member.

FIG. 4 shows, in a perspective view, the front part of the connecting rod 20 comprising the transverse grooves 15–19 into which the cams 10–14 shown in FIGS. 1 and 2 of the bristle holders 4-o engage when the insert 3 is placed into the receiver 21.

Figure 5:
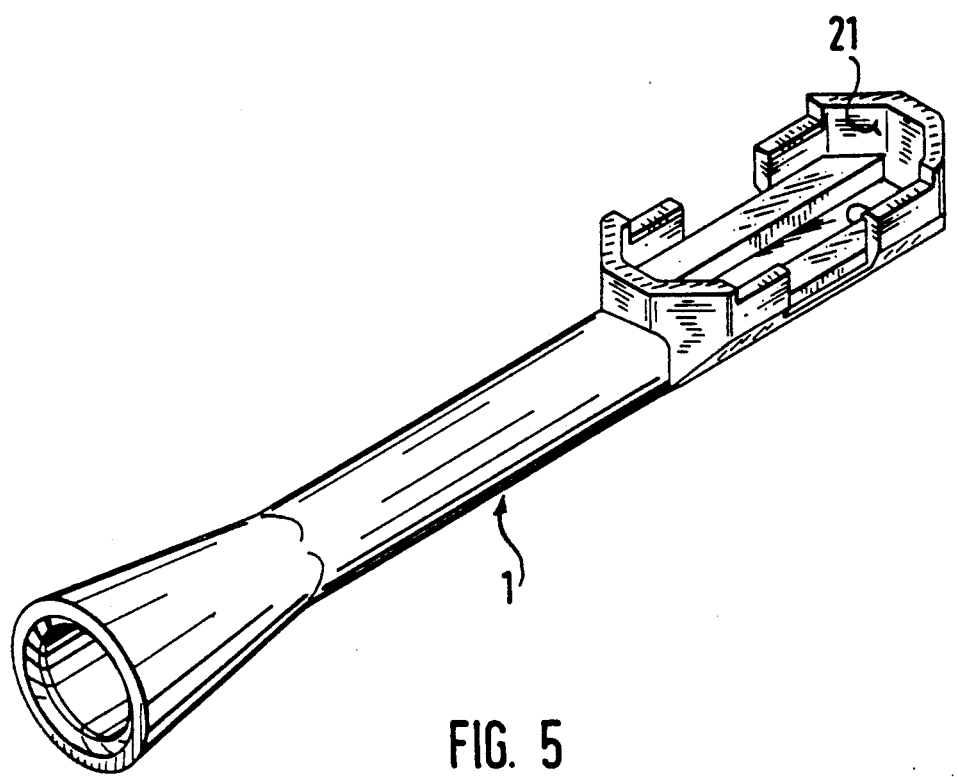
FIG. 5 shows a perspective view of the brush member without fittings.

FIG. 5 shows the brush member 1 as a whole. It can be non-detachably connected to the handle (not shown) of the toothbrush as the insert 3 with the tufts of bristles 9 can be exchanged therein.

We claim:

1. A brush member for an electric toothbrush which is connectable at its lower end to a handle of the electric toothbrush, said brush member comprising:

an exchangeable insert comprising a plurality of axially rotatable bristle holders, each of said bristle holders comprising tufts of bristles extending from an upper portion of the bristle holders and an eccentric cam extending from a bottom portion of the bristle holders;

a brush head at an upper end of the brush member, said brush head comprising means for removably receiving the exchangeable insert; and driving means for axially rotating said bristle holders, said driving means located within the brush head and comprising a plurality of substantially transverse grooves in a reciprocating connecting rod, said transverse grooves for engaging the eccentric cams of each of the bristle holders of an exchangeable insert received in the receiving means.

2. The brush member according to claim 1, wherein the receiving means comprises an opening in one side of the brush head.

3. The brush member according to claim 2, wherein the exchangeable insert further comprises means for releasably fixing the exchangeable insert within said opening.

4. The brush member according to claim 3, wherein said means for releasable fixing comprises a manually releasable snap connection.

5. The brush member according to claim 4, wherein the manually releasable snap connection comprises a catch located on a side of the exchangeable insert for engagement with a wall of the brush head.

* * * * *